US010576395B2

(12) United States Patent
Casali et al.

(10) Patent No.: US 10,576,395 B2
(45) Date of Patent: Mar. 3, 2020

(54) SUPERCRITICAL CARBON DIOXIDE EXTRACTION OF RESIDUAL GLUTARALDEHYDE FROM CROSSLINKED COLLAGEN

(71) Applicant: University of South Carolina, Columbia, SC (US)

(72) Inventors: Dominic M. Casali, Elgin, SC (US); Michael A. Matthews, Columbia, SC (US)

(73) Assignee: University of South Carolina, Columbia, SC (US)

(*) Notice: Subject to any disclaimer, the term of this patent is extended or adjusted under 35 U.S.C. 154(b) by 101 days.

(21) Appl. No.: 15/810,766

(22) Filed: Nov. 13, 2017

(65) Prior Publication Data
US 2018/0264378 A1    Sep. 20, 2018

Related U.S. Application Data

(60) Provisional application No. 62/470,981, filed on Mar. 14, 2017.

(51) Int. Cl.
*B01D 11/04* (2006.01)
*B01J 3/00* (2006.01)
*C07K 1/14* (2006.01)
*C07K 14/78* (2006.01)

(52) U.S. Cl.
CPC .......... *B01D 11/0403* (2013.01); *B01J 3/008* (2013.01); *C07K 1/145* (2013.01); *C07K 14/78* (2013.01); *Y02P 20/544* (2015.11)

(58) Field of Classification Search
CPC .... B01D 11/0403; C07K 14/78; C07K 1/145; B01J 3/008; Y02P 20/544
See application file for complete search history.

(56) References Cited

U.S. PATENT DOCUMENTS

| 5,135,766 | A | 8/1992 | Hermsen et al. |
| 2003/0153638 | A1* | 8/2003 | Lai .............................. C08J 3/24 521/53 |
| 2007/0009606 | A1 | 1/2007 | Serdy et al. |

(Continued)

OTHER PUBLICATIONS

Introduction, American Journal of Transplantation, 14 (2014).
(Continued)

*Primary Examiner* — Frances Tischler
(74) *Attorney, Agent, or Firm* — Dority & Manning, P.A.

(57) ABSTRACT

A system and method for removing residual glutaraldehyde from a natural polymer scaffold crosslinked with glutaraldehyde is provided. The system includes a cleaning solution comprising carbon dioxide and one or more polar solvents and an environmental chamber that can include and a treatment chamber. The environmental chamber is maintained at a temperature greater than 31.1° C. and the carbon dioxide is maintained at a pressure greater than 7.38 megapascals to form supercritical carbon dioxide. A crosslinked natural polymer scaffold treated via the glutaraldehyde removal system and method can have a glutaraldehyde content of less than about 3 parts per million. A crosslinked natural polymer scaffold cleaning solution comprising supercritical carbon dioxide and one or more polar solvents is also provided.

10 Claims, 4 Drawing Sheets

(56) References Cited

U.S. PATENT DOCUMENTS

2014/0205674 A1 7/2014 Wei
2015/0315540 A1 11/2015 Matthews et al.

OTHER PUBLICATIONS

F. Berthiaume, T. J. Maguire, M. L. Yarmush, Tissue Engineering and Regenerative Medicine: History, Progress, and Challenges, in: J.M. Prausnitz (Ed.) Annual Review of Chemical and Biomolecular Engineering, vol. 2, Annual Reviews, Palo Alto, 2011, pp. 403-430.
B.-S. Kim, I.-K. Park, T. Hoshiba, H. L. Jiang, Y. J. Choi, T. Akaike, C. S. Cho, Design of artificial extracellular matrices for tissue engineering, Progress in Polymer Science, 36 (2011) 238-268.
J.E. Reing, L. Zhang, J. Myers-Irvin, K.E. Cordero, D.O. Freytes, E. Heber-Katz, K. Bedelbaeva, D. Mcintosh, A. Dewilde, S.J. Braunhut, S.F. Badylak, Degradation Products of Extracellular Matrix Affect Cell Migration and Proliferation, Tissue Engineering Part A, 15 (2009) 605-614.
B.N. Brown, S.F. Badylak, Extracellular matrix as an inductive scaffold for functional tissue reconstruction, Translational Research, 163 (2014) 268-285.
B.N. Brown, R. Londono, S. Tottey, L. Zhang, K.A. Kukla, M.T. Wolf, K.A. Daly, J.E. Reing, S.F. Badylak, Macrophage phenotype as a predictor of constructive remodeling following the implantation of biologically derived surgical mesh materials, Acta Biomaterialia, 8 (2012) 978-987.
N. Syazwani, A. Azhim, Y. Morimoto, K.S. Furukawa, T. Ushida, Decellularization of Aorta Tissue Using Sonication Treatment as Potential Scaffold for Vascular Tissue Engineering, Journal of Medical and Biological Engineering, 35 (2015) 258-269.
H.W. Xu, B.S. Xu, Q. Yang, X.L. Li, X.L. Ma, Q. Xia, Y. Zhang, C.Q. Zhang, Y.H. Wu, Y.Y. Zhang, Comparison of Decellularization Protocols for Preparing a Decellularized Porcine Annulus Fibrosus Scaffold, Plos One, 9 (2014).
T.C. Evaristo, F.C.M. Da Cruzalves, A. Moroz, W. Mion, M.J. Acorci-Valerio, S.L. Felisbino, R. Rossi-Ferreira, R.L. Ruiz, E. Deffune, Light-emitting diode effects on combined decellularization of tracheae. A novel approach to obtain biological scaffolds, Acta Cirurgica Brasileira, 29 (2014) 485-492.
T.J. Keane, I.T. Swinehart, S.F. Badylak, Methods of tissue decellularization used for preparation of biologic scaffolds and in vivo relevance, Methods, 84 (2015) 25-34.
L.N. Sierad, E.L. Shaw, A. Bina, B. Brazile, N. Rierson, S.S. Patnaik, A. Kennamer, R. Odum, O. Cotoi, P. Terezia, K. Branzaniuc, H. Smallwood, R. Deac, I. Egyed, Z. Pavai, A. Szanto, L. Harceaga, H. Suciu, V. Raicea, P. Olah, A. Simionescu, J. Liao, I. Movileanu, M. Harpa, D.T. Simionescu, Functional Heart Valve Scaffolds Obtained by Complete Decellularization of Porcine Aortic Roots in a Novel Differential Pressure Gradient Perfusion System, Tissue Engineering Part C—Methods, 21 (2015) 1284-1296.
J.J.A. Barry, S.N. Nazhat, F. Rose, A.H. Hainsworth, C.A. Scotchford, S.M. Howdle, Supercritical carbon dioxide foaming of elastomer/heterocyclic methacrylate blends as scaffolds for tissue engineering, Journal of Materials Chemistry, 15 (2005) 4881-4888.
M. Floren, S. Spilimbergo, A. Motta, C. Migliaresi, Porous poly(D,L-lactic acid) foams with tunable structure and mechanical anisotropy prepared by supercritical carbon dioxide, Journal of Biomedical Materials Research Part B—Applied Biomaterials, 99B (2011) 338-349.
H.Y. Tai, M.L. Mather, D. Howard, W.X. Wang, L.J. White, J.A. Crowe, S.P. Morgan, A. Chandra, D.J. Williams, S.M. Howdle, K.M. Shakesheff, Control of pore size and structure of tissue engineering scaffolds produced by supercritical fluid processing, European Cells & Materials, 14 (2007) 64-76.
X. Liu, D.L. Yang, J.J. Liu, K. Xu, G.H. Wu, Modeling of supercritical fluid extraction of flavonoids from Calycopteris floribunda leaves, Chem. Pap., 68 (2014) 316-323.
H. Bagheri, M.Y.B. Manap, Z. Solati, Response surface methodology applied to supercritical carbon dioxide extraction of Piper nigrum L. essential oil, LWT—Food Sci. Technol., 57 (2014) 149155.
G. Ferrentino, S. Spilimbergo, High pressure carbon dioxide pasteurization of solid foods: Current knowledge and future outlooks, Trends in Food Science & Technology, 22 (2011) 427-441.
G. Ferrentino, A. Belscak-Cvitanovic, D. Komes, S. Spilimbergo, Quality Attributes of Fresh-Cut Coconut after Supercritical Carbon Dioxide Pasteurization, Journal of Chemistry, (2013).
G. Ferrentino, S. Balzan, S. Spilimbergo, On-line color monitoring of solid foods during supercritical $CO_2$ pasteurization, Journal of Food Engineering, 110 (2012) 80-85.
A. Jimenez, J. Zhang, M.A. Matthews, Evaluation of $CO_2$-Based Cold Sterilization of a Model Hydrogel, Biotechnology and Bioengineering, 101 (2008) 1344-1352.
P.J. Tarafa, A. Jimenez, J.A. Zhang, M.A. Matthews, Compressed carbon dioxide ($CO_2$) for decontamination of biomaterials and tissue scaffolds, Journal of Supercritical Fluids, 53 (2010) 192-199.
J. Zhang, T.A. Davis, M.A. Matthews, M.J. Drews, M. Laberge, Y.H.H. An, Sterilization using high-pressure carbon dioxide, Journal of Supercritical Fluids, 38 (2006) 354-372.
K. Sawada, D. Terada, T. Yamaoka, S. Kitamura, T. Fujisato, Cell removal with supercritical carbon dioxide for acellular artificial tissue, Journal of Chemical Technology and Biotechnology, 83 (2008) 943-949.
S.B. Lumpkins, N. Pierre, P.S. Mcfetridge, A mechanical evaluation of three decellularization methods in the design of a xenogeneic scaffold for tissue engineering the temporomandibular joint disc, Acta Biomaterialia, 4 (2008) 808-816.
E. Sachlos, D.A. Wahl, J.T. Triffitt, J.T. Czernuszka, the impact of critical point drying with liquid carbon dioxide on collagen-hydroxyapatite composite scaffolds, Acta Biomaterialia, 4 (2008) 1322-1331.
P.J. Shah, Z. Wu, A.M. Sarangan, Effects of $CO_2$ critical point drying on nanostructured $SiO_2$ thin films after liquid exposure, Thin Solid Films, 527 (2013) 344-348.
H. Halbritter, Preparing living pollen material for scanning electron microscopy using 2,2-dimethoxypropane (DMP) and critical-point drying, Biotech. Histochem., 73 (1998) 137-143.
S. Funamoto, K. Nam, T. Kimura, A. Murakoshi, Y. Hashimoto, K. Niwaya, S. Kitamura, T. Fujisato, A. Kishida, The use of high-hydrostatic pressure treatment to decellularize blood vessels, Biomaterials, 31 (2010) 3590-3595.
Abstract of J.W. Lee, E. Fukusaki, T. Bamba, Application of supercritical fluid carbon dioxide to the extraction and analysis of lipids, Bioanalysis, 4 (2012) 2413-2422.
L. Baldino, S. Concilio, S. Cardea, I. De Marco, E. Reverchon, Complete glutaraldehyde elimination during chitosan hydrogel drying by SC—$CO_2$ processing, Journal of Supercritical Fluids, 103 (2015) 70-76.
L. Baldino, S. Cardea, I. De Marco, E. Reverchon, Chitosan scaffolds formation by a supercritical freeze extraction process, The Journal of Supercritical Fluids, 90 (2014) 27-34.
A. Zambon, M. Vetralla, L. Urbani, M.F. Pantano, G. Ferrentino, M. Pozzobon, N.M. Pugno, P. De Coppi, N. Elvassore, S. Spilimbergo, Dry acellular oesophageal matrix prepared by supercritical carbon dioxide, Journal of Supercritical Fluids, 115 (2016) 33-41.
P.M. Crapo, T.W. Gilbert, S.F. Badylak, An overview of tissue and whole organ decellularization processes, Biomaterials, 32 (2011) 3233-3243.
T.W. Gilbert, T.L. Sellaro, S.F. Badylak, Decellularization of tissues and organs, Biomaterials, 27 (2006) 3675-3683.
J.C. Liu, B.X. Han, H.L. Zhang, G.Z. Li, X.G. Zhang, J. Wang, B.Z. Dong, Formation of water-in-$CO_2$ microemulsions with non-fluorous surfactant Ls-54 and solubilization of biomacromolecules, Chemistry—a European Journal, 8 (2002) 1356-1360.
P.J. Tarafa, E. Williams, S. Panvelker, J.Z. Zhang, M.A. Matthews, Removing endotoxin from metallic biomaterials with compressed carbon dioxide-based mixtures, Journal of Supercritical Fluids, 55 (2011) 1052-1058.

(56) References Cited

OTHER PUBLICATIONS

P.J. Tarafa, M.A. Matthews, Phase equilibrium for surfactant Ls-54 in liquid CO2 with water and solubility estimation using the Peng-Robinson equation of state, Fluid Phase Equilibria, 298 (2010) 212-218.
Gumerov, et al. "Solubility in Supercritical Carbon Dioxide" High Temperature, vol. 40, No. 2, 2002 pp. 231-234.
Yost Mt, L.; Price, R.L.: Collagen Processing. In: Encyclopedia of Biomaterials and Biomedical Engineering. Edited by Wnek GEB, G.L., 2nd ed. edn: Taylor & Francis; 2004.
Huang GP, Shanmugasundaram S, Masih P, Pandya D, Amara S, Collins G, Arinzeh TL: An investigation of common crosslinking agents on the stability of electrospun collagen scaffolds. Journal of Biomedical Materials Research Part A 2015, 103(2):762-771.
Lowe CJ, Reucroft IM, Grota MC, Shreiber DI: Production of highly aligned collagen scaffolds by freeze-drying of self-assembled, fibrillar collagen gels. Acs Biomaterials—Science & Engineering 2016, 2(4):643-651.
Rodriguez-Rivera V, Weidner JW, Yost MJ: Three-dimensional biomimetic technology: novel biorubber creates defined micro- and macro-scale architectures in collagen hydrogels. Jove—Journal of Visualized Experiments 2016(108).
Chevallay B, Herbage D: Collagen-based biomaterials as 3D scaffold for cell cultures: applications for tissue engineering and gene therapy. Medical & Biological Engineering & Computing 2000, 38(2):211-218.
Yost MJ, Baicu CF, Stonerock CE, Goodwin RL, Price RL, Davis JM, Evans H, Watson PD, Gore CM, Sweet J et al: A novel tubular scaffold for cardiovascular tissue engineering. Tissue Engineering 2004, 10(1-2):273-284.
Dong CJ, LV YG: Application of collagen scaffold in tissue engineering: Recent advances and new perspectives. Polymers 2016, 8(2).
Liu YY, Ma L, Gao CY: Facile fabrication of the glutaraldehyde cross-linked collagen/chitosan porous scaffold for skin tissue engineering. Materials Science & Engineering C-Materials for Biological Applications 2012, 32(8):2361-2366.
Balasubramanian P, Roether JA, Schubert DW, Beier JP, Boccaccini AR: Bi-layered porous constructs of PCL-coated 45S5 bioactive glass and electrospun collagen-PCL fibers. Journal of Porous Materials 2015, 22(5):1215-1226.
Venkatesan J, Pallela R, Kim SK: Applications of carbon nanomaterials in bone tissue engineering. Journal of Biomedical Nanotechnology 2014, 10(10):3105-3123.
Calabrese G, Giuffrida R, Fabbi C, Figallo E, Lo Furno D, Gulino R, Colarossi C, Fullone F, Giuffrida R, Parenti R et al: Collagen-Hydroxyapatite scaffolds induce human adipose derived stem cells osteogenic differentiation in vitro. Plos One 2016, 11(3).
Weadock KS, Miller EJ, Bellincampi LD, Zawadsky JP, Dunn MG: Physical cross-linking of collagen fibers—comparison of ultraviolet-irradiation and dehydrothermal treatment. Journal of Biomedical Materials Research 1995, 29(11):1373-1379.
Damink L, Dijkstra PJ, Vanluyn MJA, Vanwachem PB, Nieuwenhuis P, Feijen J: Glutaraldehyde as a cross-linking agent for collagen-based biomaterials. Journal of Materials Science-Materials in Medicine 1995, 6(8):460-472.
Speer DP, Chvapil M, Eskelson CD, Ulreich J: Biological effects of residual glutaraldehyde in glutaraldehyde-tanned collagen biomaterials. Journal of Biomedical Materials Research 1980, 14(6):753-764.
Zeiger E, Gollapudi B, Spencer P: Genetic toxicity and carcinogenicity studies of glutaraldehyde—a review. Mutation Research/Reviews in Mutation Research 2005, 589(2):136-151.
Yang C, Wu XM, Zhao YH, Xu L, Wei SC: Nanofibrous scaffold prepared by electrospinning of poly(vinyl alcohol)/gelatin aqueous Solutions. Journal of Applied Polymer Science 2011, 121(5):3047-3055.
Yang CR: Enhanced physicochemical properties of collagen by using EDC/NHS-crosslinking. Bulletin of Materials Science 2012, 35(5):913-918.
Liu TX, Wang Z: Collagen crosslinking of porcine sclera using genipin. Acta Ophthalmologica 2013, 91(4):E253-E257.
Grunert P, Borde BH, Towne SB, Moriguchi Y, Hudson KD, Bonassar LJ, Hartl R: Riboflavin crosslinked high-density collagen gel for the repair of annular defects in intervertebral discs: An in vivo study. Acta Biomaterialia 2015, 26:215-224.
Joshi R, Babu GDK, Gulati A: Effect of decaffeination conditions on quality parameters of Kangra orthodox black tea. Food Research International 2013, 53(2):693-703.
Spilimbergo S, Mantoan D, Quaranta A, Della Mea G: Real-time monitoring of cell membrane modification during supercritical CO2 pasteurization. Journal of Supercritical Fluids 2009, 48(1):93-97.
Abstract of An YH, Alvi FI, Kang Q, Laberge M, Drews MJ, Zhang J, Matthews MA, Arciola CR: Effects of sterilization on implant mechanical property and biocompatibility. Int J Artif Organs 2005, 28(11):1126-1137.
Zhang J, Burrows S, Gleason C, Matthews MA, Drews MJ, Laberge M, An YHH: Sterilizing Bacillus pumilus spores using supercritical carbon dioxide. J Microbiol Methods 2006, 66(3):479-485.
Zhang J, Dalal N, Gleason C, Matthews MA, Waller LN, Fox KF, Fox A, Drews MJ, Laberge M, An YH: On the mechanisms of deactivation of Bacillus atrophaeus pores using supercritical carbon dioxide. Journal of Supercritical Fluids 2006, 38(2):268-273.
Hemmer JD, Drews MJ, Laberge M, Matthews MA: Sterilization of bacterial spores by using supercritical carbon dioxide and hydrogen peroxide. Journal of Biomedical Materials Research Part B—Applied Biomaterials 2007, 80B(2):511-518.
Zhang J, Dalal N, Matthews MA, Waller LN, Saunders C, Fox KF, Fox A: Supercritical carbon dioxide and hydrogen peroxide spore structures associated with high killing rate cause mild changes in of Bacillus anthracis. J Microbiol Methods 2007, 70(3):442-451.
Weadock K, Olson RM, Silver FH: Evaluation of collagen crosslinking techniques. Biomaterials Medical Devices and Artificial Organs 1983, 11(4):293-318.
Bigi A, Cojazzi G, Panzavolta S, Rubini K, Roveri N: Mechanical and thermal properties of gelatin films at different degrees of glutaraldehyde crosslinking. Biomaterials 2001, 22(8):763-768.
Cheung DT, Nimni ME: Mechanism of crosslinking of proteins by glutaraldehyde 2. Reaction with monomeric and polymeric collagen. Connective Tissue Research 1982, 10(2):201-216.
Kornyshev AA, Leikin S: Theory of interaction between helical molecules. Journal of Chemical Physics 1997, 107(9):3656-3674.
Cen L, Liu W, Cui L, Zhang WJ, Cao YL: Collagen tissue engineering: Development of novel biomaterials and applications. Pediatric Research 2008, 63(5):492-496.
Casali DM, Matthews MA: Decellularization of porcine aorta using supercritical carbon dioxide. In: AIChE Annual Meeting: 2016; San Francisco, CA.
Zhou B, Rachev A, Shazly T: The biaxial active mechanical properties of the porcine primary renal artery. Journal of the Mechanical Behavior of Biomedical Materials 2015, 48:28-37.

* cited by examiner

SUPERCRITICAL CARBON DIOXIDE EXTRACTION OF RESIDUAL GLUTARALDEHYDE FROM CROSSLINKED COLLAGEN

RELATED APPLICATIONS

The present application claims priority to U.S. Provisional Application Ser. No. 62/470,981, filed on Mar. 14, 2017, which is incorporated herein in its entirety by reference thereto.

BACKGROUND

Since the emergence of tissue engineering as a scientific field, collagen has been used as a biomaterial for tissue engineered scaffolds. As a protein found ubiquitously throughout the human body, collagen has very low immunogenicity and antigenicity. Collagen can be molded into scaffolds of various sizes and morphologies in both the solid and liquid/gel state; some examples of this include electrospun scaffolds, lyophilized collagen scaffolds, and collagen hydrogel scaffolds. Methods used to form such collagen scaffolds allow the collagen scaffolds to be tailored to have a desired porosity and permeability. Furthermore, collagen has been shown to be an influential factor in orchestrating the adhesion, migration, and proliferation of cells during tissue growth. In addition, collagen scaffolds also evoke a less disruptive immune response than many synthetic polymers.

However, collagen does have one major weakness as a tissue engineered scaffold material—its lack of mechanical strength. Because of this deficiency, untreated collagen is rarely used as the sole material in the fabrication of tissue engineered scaffolds. There are two approaches commonly utilized to circumvent this problem. The first involves using a second biomaterial in conjunction with collagen to create a collagen blend. A number of materials have been used, including natural polymers, synthetic polymers, carbon nanotubes, and ceramics. This approach increases the mechanical strength of the collagen scaffolds but also risks increasing immunogenicity. This approach also increases the complexity of scaffold design and post-fabrication processing steps, such as sterilization and removal of residuals.

The other approach is crosslinking collagen to augment its mechanical strength. Crosslinks are covalent bonds formed between adjacent polymer chains that increase the mechanical strength of a polymer. Such bonding can be photo-activated using ultraviolet (UV) irradiation, but UV crosslinking can denature proteins and is ineffective for thick samples because of its non-uniform penetration depth. Chemical crosslinking is often more effective; in particular, glutaraldehyde is a reagent that has been shown to achieve a high degree of crosslinking at relatively low concentrations. However, residual glutaraldehyde is extremely cytotoxic. For example, it has been shown that a little as 3 parts per million (ppm) residual glutaraldehyde can kill over 99% of fibroblasts, and glutaraldehyde is also a known carcinogen. Moreover, crosslinked tissue engineered structures often must undergo a rigorous heating process at temperatures as high as 120° C. for a period of up to about 12 hours to remove residual reagents, which can be detrimental to the desired physical and biochemical properties of collagen scaffolds. For instance, the standard heating process to remove residual glutaraldehyde from a gel scaffold can exceed the glass transition temperature of the material and cause collapse of the aerogel structure. Recently, more attention has been given to collagen blends and to alternative crosslinking agents, such as 1-ethyl-3-(3-(dimethylamino)propyl)carbodiimide (EDC), genipin, and riboflavin.

However, if residual glutaraldehyde were removed using a faster and less disruptive method at a lower temperature where the resulting crosslinked natural polymer scaffolds maintained their mechanical and thermal stability, which is important for preserving scaffold functionality in downstream applications, it could significantly benefit the field of tissue engineering. As such, a need exists for a system and method of removing residual glutaraldehyde from crosslinked tissue engineered scaffolds including collagen, any other natural polymer (e.g., elastin, fibrinogen, or gelatin), or a combination thereof.

SUMMARY OF THE INVENTION

In one embodiment of the present invention, a system for removing residual glutaraldehyde from a natural polymer scaffold crosslinked with glutaraldehyde is provided. The system includes a cleaning solution comprising carbon dioxide and one or more polar solvents, and an environmental chamber comprising a treatment chamber, wherein the environmental chamber is maintained at a temperature greater than 31.1° C. and the carbon dioxide is maintained at a pressure greater than 7.38 megapascals to form supercritical carbon dioxide.

In another embodiment, the treatment chamber can receive the natural polymer scaffold.

In one embodiment, the environmental chamber can include a presaturation chamber, wherein the cleaning solution can be mixed in the presaturation chamber.

In one more embodiment, the cleaning solution can be deliverable from the presaturation chamber to the treatment chamber.

In still another embodiment, the system can include a pump, wherein the pump compresses the carbon dioxide.

In yet another embodiment, the cleaning solution can be delivered to the treatment chamber at a flow rate ranging from about 1.5 millimeters per minute to about 3.5 milliliters per minute.

In still another embodiment, the system can facilitate removal of the residual glutaraldehyde from the natural polymer scaffold so that glutaraldehyde is present in the natural polymer scaffold at a level of less than about 3 parts per million after the natural polymer scaffold is treated with the cleaning solution.

In an additional embodiment, the natural polymer scaffold can include collagen, elastin, fibrinogen, gelatin, or a combination thereof. For instance, the natural polymer scaffold can include collagen.

In one more embodiment, the one or more polar solvents can include ethanol, methanol, isopropanol, water, acetic acid, or a combination thereof.

In another particular embodiment of the present invention, a method for removing residual glutaraldehyde from a natural polymer scaffold is provided. The method includes treating the natural polymer scaffold with a cleaning solution comprising carbon dioxide and one or more polar solvents at a temperature greater than 31.1° C., wherein the carbon dioxide is maintained at a pressure greater than 7.38 megapascals to form supercritical carbon dioxide.

In one embodiment, a pump can compress the carbon dioxide before the carbon dioxide is delivered to the natural polymer scaffold.

In another embodiment, the carbon dioxide and the one or more polar solvents can be mixed for a time period ranging from about 5 seconds to about 10 minutes prior to exposing the natural polymer scaffold to the cleaning solution.

Further, the one or more polar solvents can include ethanol, methanol, isopropanol, water, acetic acid, or a combination thereof.

In an additional embodiment, the cleaning solution can be delivered to a treatment chamber containing the natural polymer scaffold. Moreover, the cleaning solution can be delivered to the treatment chamber at a flow rate ranging from about 1.5 millimeters per minute to about 3.5 milliliters per minute.

In one more embodiment, the cleaning solution can be mixed in a presaturation chamber, and the cleaning solution can be delivered from the presaturation chamber to a treatment chamber containing the natural polymer scaffold.

In still another embodiment, the natural polymer scaffold can be exposed to the cleaning solution for a time period ranging from about 1 minute to about 2 hours.

In yet another embodiment, treating the natural polymer scaffold with the cleaning solution can result in the natural polymer scaffold having a denaturation temperature of greater than about 60° C. in 4% acetic acid.

In an additional embodiment, treating the natural polymer scaffold with the cleaning solution can result in the natural polymer scaffold having an ultimate tensile strength that is greater than about 40 kilopascals when the natural polymer scaffold includes collagen.

In one more embodiment, the method can facilitate removal of the residual glutaraldehyde from the natural polymer scaffold so that glutaraldehyde is present in the natural polymer scaffold at a level of less than about 3 parts per million after the natural polymer scaffold is treated with the cleaning solution.

In one more embodiment of the present invention, a cleaning solution for removing residual glutaraldehyde from a natural polymer scaffold is contemplated. The cleaning solution includes supercritical carbon dioxide and one or more polar solvents (e.g., ethanol). The glutaraldehyde is present in the natural polymer scaffold at a level of less than about 3 parts per million after the natural polymer scaffold is exposed to the cleaning solution for a time period ranging from about 1 minute to about 2 hours.

Other features and aspects of the present invention are set forth in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

Figure 1:
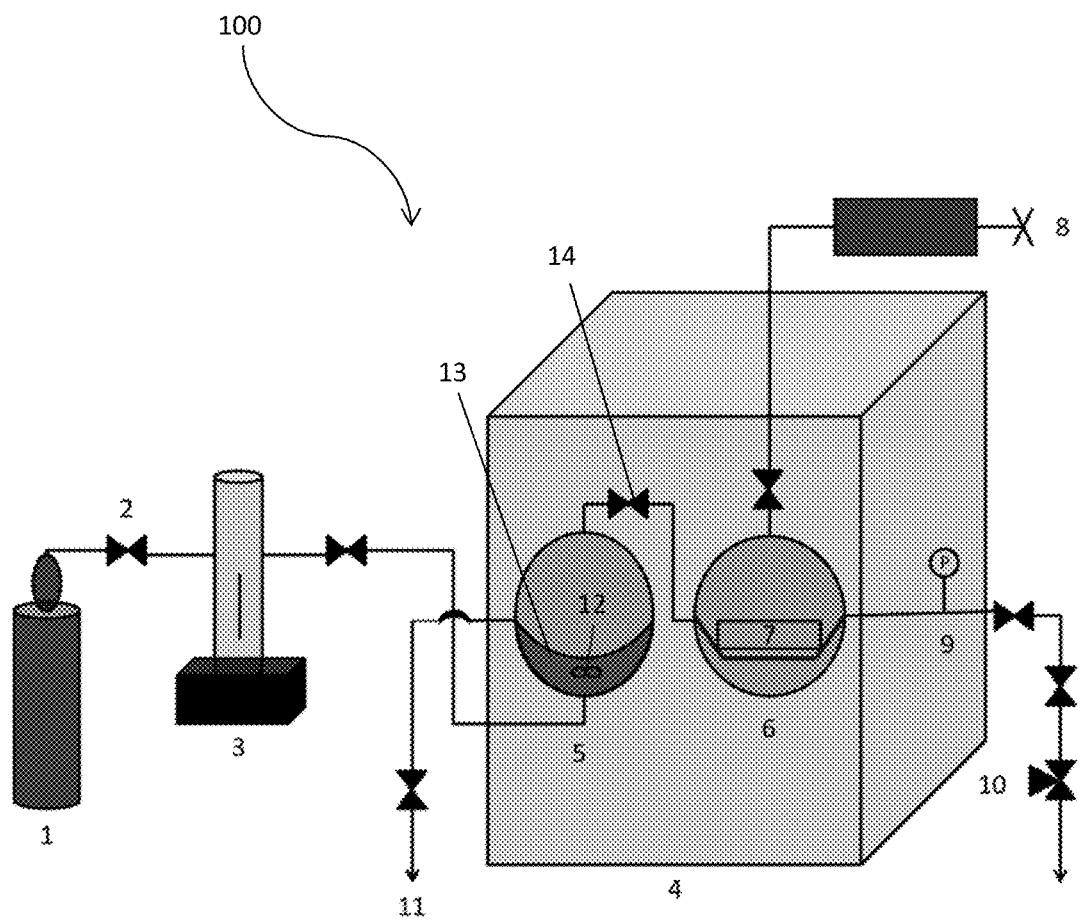
FIG. 1 shows a schematic of a two-chamber supercritical carbon dioxide flow system according to one particular embodiment of the present invention.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

The present invention is directed to a system and method for extracting residual glutaraldehyde from a crosslinked natural polymer scaffold using supercritical carbon dioxide ($CO_2$) and one or more polar solvents (e.g., ethanol, methanol, isopropanol, water, acetic acid, or a combination thereof), thereby allowing for improved cell seeding and increased viability of cells seeded onto the scaffolds in tissue engineering applications. A natural polymer scaffold cleaning solution containing supercritical $CO_2$ and one or more polar solvents (e.g., ethanol, methanol, isopropanol, water, acetic acid, or a combination thereof) is also contemplated by the present invention. Supercritical $CO_2$ is formed when pure $CO_2$ is heated and pressurized above the critical conditions of 31.1° C. and 7.38 megapascals (MPa). In particular, the system contemplated by the present invention is a dynamic carbon dioxide flow system that is used to extract glutaraldehyde from tissue engineering scaffolds composed of a crosslinked natural polymer such as collagen, elastin, fibrinogen, gelatin, or a combination thereof, thus greatly reducing the cytotoxicity of the resulting crosslinked scaffold. The system and method of the present invention allows for a fast, safe method of glutaraldehyde extraction that maintains the natural scaffold's mechanical and biochemical integrity. Additionally, exposure to supercritical $CO_2$ at the conditions used is known to cause high-level disinfection, removing microbial contaminants from the matrix. In one particular embodiment, the scaffold can be a crosslinked collagen scaffold.

The system and method of the present invention contemplate the use of high pressure vessels, which can be made of stainless steel or any other suitable material, an environmental chamber, a back-pressure regulator, and a pump (e.g., a syringe pump or any other suitable pump). In one particular embodiment, the environmental chamber, back-pressure regulator, and pump maintain constant conditions within the system. For instance, the environmental chamber can be maintained at a temperature greater than about 31.1° C. as required to form supercritical $CO_2$. For instance, the temperature can range from about 35° C. to about 39° C., such as from about 36° C. to about 38° C., such as from about 36.5° C. to about 37.5° C. Further, the pressure in the system can be maintained at a level above about 73.8 bar (7.38 megapascals) as required to form supercritical $CO_2$. For example, the pressure in the system can range from about 150 bar (15 megapascals) to about 250 bar (25 megapascals), such as from about 175 bar (17.5 megapascals) to about 225 bar (22.5 megapascals), such as from about 190 bar (19 megapascals) to about 210 bar (21 megapascals). In addition, the $CO_2$ flow rate can range from about 1.5 milliliters per minute to about 3.5 milliliters per minute, such as from about 1.75 milliliters per minute to about 3.25 milliliters per minute, such as from about 2 milliliters per minute to about 3 milliliters per minute. In other words, for a treatment chamber having a volume of 10 milliliters, for example, the residence time of the $CO_2$ and one or more polar solvents (e.g., ethanol, methanol, isopropanol, water, acetic acid, or a combination thereof) can range from about 2 minutes to about 7 minutes, such as from about 3 minutes to about 6 minutes, such as from about 4 minutes to about 5 minutes.

In one particular embodiment, the environmental chamber can be maintained at a temperature of about 37° C., the pressure can be maintained at 200 bar (20 megapascals), and the $CO_2$ flow rate can be maintained at about 2.5 milliliters per minute. In an additional embodiment, the environmental chamber can include a first pressure vessel (e.g., a presaturation chamber) and a second pressure vessel (e.g., a treatment chamber), where $CO_2$ is continually mixed with the polar solvent (e.g., ethanol) using a magnetic stirrer to form a $CO_2$/polar solvent solution. The resulting polar $CO_2$/polar solvent cleaning solution is then introduced into the second pressure vessel, where it dissolves residual glutaraldehyde that is present in the crosslinked collagen matrix or scaffold. However, it is also to be understood that the present invention contemplates an environmental chamber that includes a single pressure vessel (e.g., a treatment chamber), where the $CO_2$/polar solvent cleaning solution is delivered to the treatment chamber with, for example, two pumps (e.g., syringe pumps). In such an embodiment, one pump delivers the liquid $CO_2$ to the treatment chamber and the other pump delivers the polar solvent to the treatment chamber at predetermined ratios to deliver the appropriate concentration of each component of the cleaning solution to the treatment chamber. In another embodiment, it is contemplated that an injection loop can be used to deliver the cleaning solution directly to the treatment chamber.

Specifically, and referring to FIG. 1, in one particular embodiment, the residual glutaraldehyde removal system 100 of the present invention can include a supply of liquid carbon dioxide 1, a high pressure valve 2, a pump 3 (e.g., a syringe pump), an environmental chamber 4, a presaturation chamber 5 containing a stir bar 12 to mix the $CO_2$ and polar solvent (e.g., ethanol) to form a cleaning solution 13, a treatment chamber 6 containing a crosslinked natural polymer scaffold 7, a $CO_2$ hand pump 8, a pressure gauge 9, a back pressure regulator 10, a treatment chamber valve 14, and an emergency vent 11.

Generally, to remove residual glutaraldehyde from a crosslinked natural polymer scaffold 7 such as a crosslinked collagen scaffold, the scaffold 7 is loaded into the treatment chamber 6 of the residual glutaraldehyde removal system 100. The treatment chamber 6 is located in an environmental chamber 4. Then, liquid carbon dioxide 1 can be compressed in a chilled syringe pump 3 or any other suitable pump and slowly bubbled into a first high pressure vessel, which can be referred to as the presaturation chamber 5, which is also located in the environmental chamber 4. In the presaturation chamber 5, one or more polar solvents (e.g., ethanol) can be mixed with the carbon dioxide 1 using a stir bar 12 until the one or more polar solvents (e.g., ethanol) is fully dissolved in the carbon dioxide 1 to form the cleaning solution 13. The carbon dioxide 1 and one or more polar solvents (e.g., ethanol) can be mixed for a time period ranging from about 5 seconds to about 10 minutes, such as from about 10 seconds to about 8 minutes, such as from about 15 seconds to about 4 minutes. In one particular embodiment, the carbon dioxide and one or more polar solvents (e.g., ethanol) can be mixed for a time period of about 1 minute. Next, the valve 14 to the treatment chamber 6, which contains the natural polymer scaffold 7 to be treated, can be opened, and the $CO_2$ flow through the treatment chamber 6 at a rate ranging from about 1.5 milliliters per minute to about 3.5 milliliters per minute, such as from about 1.75 milliliters per minute to about 3.25 milliliters per minute, such as from about 2 milliliters per minute to about 3 milliliters per minute. In other words, for a treatment chamber having a volume of 10 milliliters, for example, the residence time of the $CO_2$ and one or more polar solvents (e.g., ethanol) can range from about 2 minutes to about 7 minutes, such as from about 3 minutes to about 6 minutes, such as from about 4 minutes to about 5 minutes. In addition, the scaffold 7 can be treated for a time frame ranging from about 1 minute to about 2 hours, such as from about 2 minutes to about 90 minutes, such as from about 4 minutes to about 60 minutes. In one particular embodiment, the scaffold 7 can be treated for about 60 minutes.

Moreover, the temperature can be maintained at a temperature greater than 31.1° C. by the environmental chamber 4 and the pressure of the $CO_2$ in the vessels can be maintained at a level greater than about 7.38 megapascals (e.g., at about 20 megapascals) using a 6000 psi back-pressure regulator 10 in order to maintain the carbon dioxide 1 in a supercritical state. A manual hand pump 8 can be used to depressurize the system 100 at a rate ranging from about 0.1 megapascals per minute to about 0.6 megapascals per minute, such as from about 0.2 megapascals per minute to about 0.5 megapascals per minute, such as from about 0.3 megapascals per minute to about 0.4 megapascals per minute. For instance, the system 100 can be depressurized at a rate of about 0.34 megapascals per minute (50 psi/minute). It is to be understood that various valves (e.g., high pressure valve 2, valve 14) and fittings (e.g., back pressure regulator 10) rated for pressures up to 68.9 MPa can be used throughout the system 100.

In any event, natural polymer scaffolds treated in the residual glutaraldehyde removal system according to the method described herein can have a glutaraldehyde content of less than about 3 parts per million (ppm) after treatment with supercritical $CO_2$ and polar solvent (e.g., ethanol) cleaning solution. For instance, the treated natural polymer scaffolds can have a glutaraldehyde content of less than about 2 ppm, such as less than about 1.5 ppm, such as less than about 1 ppm. In one particular embodiment, the treated natural polymer scaffolds can have a glutaraldehyde content of less than about 0.8 ppm. Further, the treated natural polymer scaffold can have a denaturation temperature that is greater than about 50° C., such as greater than about 60° C., such as greater than about 65° C. in 4% acetic acid. Moreover, the treated natural polymer scaffold (e.g., collagen scaffold) can have an ultimate tensile strength that is greater than about 40 kilopascals, such as greater than about 60 kilopascals, such as greater than about 100 kilopascals. For instance, the ultimate tensile strength can range from about 100 kilopascals to about 1500 kilopascals, such as from about 200 kilopascals to about 1200 kilopascals. The present invention may be better understood with reference to the following example.

EXAMPLE 1

Example 1 demonstrates the ability to remove residual glutaraldehyde from crosslinked natural polymer scaffolds (e.g., crosslinked collagen films) using the system and method of the present invention.

Materials and Methods

Fabrication of Collagen Films

A 1% (w/v) type I collagen dispersion was obtained. Collagen films were prepared according to the protocol described in Weadock K, et al., Evaluation of collagen crosslinking techniques, *Biomaterials Medical Devices and Artificial Organs*, 1983, 11(4): 293-318. 1 molar (M) hydrochloric acid was added to 3 milliliter (mL) aliquots of collagen until a pH of 2 was reached. The acidic collagen was poured into a 35 millimeter (mm) diameter petri dish (BD Falcon, Tewksbury, Mass.), covered with aluminum foil, and air-dried in a chemical fume hood for 48 hours. The resulting dried film was then carefully removed using fine forceps, cut into 2 centimeter (cm) by 0.5 cm rectangular strips, and stored at room temperature pending further experimentation.

Glutaraldehyde and UV Crosslinking

To crosslink the collagen films, two methods were used: chemical crosslinking with glutaraldehyde and physical crosslinking with UV light. For chemical crosslinking, a 25% (v/v) glutaraldehyde solution (TCI America, Portland, Oreg.) was diluted with deionized water to either 0.25% or 1%, as desired. A collagen film strip was carefully immersed in the solution, which was vortexed for 1 min at high speed to ensure uniform mixing. The film and glutaraldehyde solution were left undisturbed for 72 hours, then the film was removed and washed several times with deionized water before further treatment.

For UV crosslinking, films were placed on an aluminum sheet 6 inches away from a 30 watt (W) ultraviolet germicidal light (General Electric, Fairfield, Conn.) for 2, 4, or 12 hours, as desired. Crosslinked films were then removed from the UV light and stored at room temperature.

Supercritical $CO_2$ Treatment

After crosslinking, the collagen films were loaded into the treatment chamber of a two-chamber supercritical $CO_2$ flow system 100, as shown in FIG. 1 and as generally described above. Liquid carbon dioxide 1 (bone-dry grade with siphon tube, 99.8% purity, Airgas National Welders, Charlotte, N.C.) was compressed in a chilled syringe pump 3 (500 HP Series, ISCO Inc., Lincoln, Nebr.) and slowly bubbled into the first high pressure vessel, called the presaturation chamber 5 (Waters Corp., Milford, Mass.). Here, ethanol was mixed with $CO_2$ using a stir bar 12 until the ethanol was fully dissolved in the carbon dioxide 1 to form a cleaning solution 13 (approximately 1 minute). Then, the valve 14 to the treatment chamber 6, which contains the collagen film to be treated 7, was opened, and $CO_2$ flow was set to 2.5 millimeters/minute (residence time: 4 minutes for a vessel having a volume of 10 milliliters).

The temperature was maintained at 37° C. by the environmental chamber 4 (LU-113 model, ESPEC Corp., Osaka, Japan), and the pressure of the supercritical $CO_2$ in the vessels was maintained at 20 megapascals (2901 psi) using a 6000 psi back-pressure regulator 10 (TESCOM, Elk River, Minn.). A manual hand pump 8 (Pressure Generator 62-6-10, High Pressure Co.) was used to depressurize the system at a rate of 0.34 megapascals/minute (50 psi/minute). Valves and fittings rated for pressures up to 68.9 megapascals (High Pressure Co., Erie, Pa.) were used throughout the system 100 (e.g., high pressure valve 2, valve 14, back pressure regulator 10, etc.).

Measurement of Residual Glutaraldehyde

Next, the concentration of residual glutaraldehyde was measured using a spectrophotometric method. Treated and untreated (but already crosslinked) collagen films were placed in a quartz cuvette (VWR, Radnor, Pa.) and filled with 3 milliliters of phosphate buffered saline (PBS) containing 0.1 molar (M) glycine. The presence of glycine has been shown to counteract the gradual pH drop normally observed with proteins in PBS solutions.

The cuvette was immediately placed into a spectrophotometer (Beckman-Coulter DU 730, Brea, Calif.), which was utilized in Kinetic/Time mode to read the absorbance of the solution every 1 minute. Typically, glutaraldehyde was released from the film over the course of 2-4 hours, although measurements were taken for up to 12 hours. In this regard, the measurements can be taken until the absorbance reading plateaus. Separately, a standard curve was generated for known concentrations of glutaraldehyde in the PBS/glycine solution, and the standard curve was used to determine the unknown concentration of residual glutaraldehyde in each film.

Differential Scanning Calorimetry

Crosslinked films were also tested both before and after $CO_2$ treatment using differential scanning calorimetry (DSC) to analyze their thermal stability. Films were cut into small pieces and dissolved in 4% acetic acid or 0.01 molar (M) hydrochloric overnight under gentle stirring. Collagen solutions were next degassed for 15 minutes using a vacuum desiccator and magnetic stirring bar. The degassed collagen solution was pipetted into to the sample port of the Nano DSC (TA Instruments, New Castle, Del.) after performing a baseline scan with the acid as the reference solution. The instrument was pressurized to 3 atm (gauge pressure) and the sample was heated from 10 to 90° C. at 2° C./minute. Data were obtained using instrument-associated RunDSC and NanoAnalyze software and then were exported to Excel for further study.

Tensile Testing

A uniaxial tensile test was used to analyze the modulus of elasticity (MOE) and ultimate tensile strength (UTS) of collagen films before and after supercritical $CO_2$ treatment. Collagen films were loaded onto a Bose 3230 Electroforce Biomechanical Tester (Bose Corp., Farmingham, Mass.) and one end was stretched at a rate of 0.01 millimeters/second until failure. The accompanying Wintest 4.1 software was used to control the experiment and collect data, which was exported to Excel for further analysis.

Statistical Analysis

Graphs and tables display the mean value plus or minus one standard deviation. A Student's t-test was used to determine statistical differences between groups. 99% confidence ($p<0.01$) was determined to be statistically significant.

Results and Discussion

Collagen films were prepared and crosslinked with either UV light or glutaraldehyde as described above. Crosslinked films were used as controls or treated with supercritical $CO_2$ for 1 hour to extract unreacted glutaraldehyde. Treated films were examined for extent of glutaraldehyde removal and for any changes in their physical properties possibly caused by supercritical $CO_2$ treatment.

Glutaraldehyde Extraction

Figure 2:
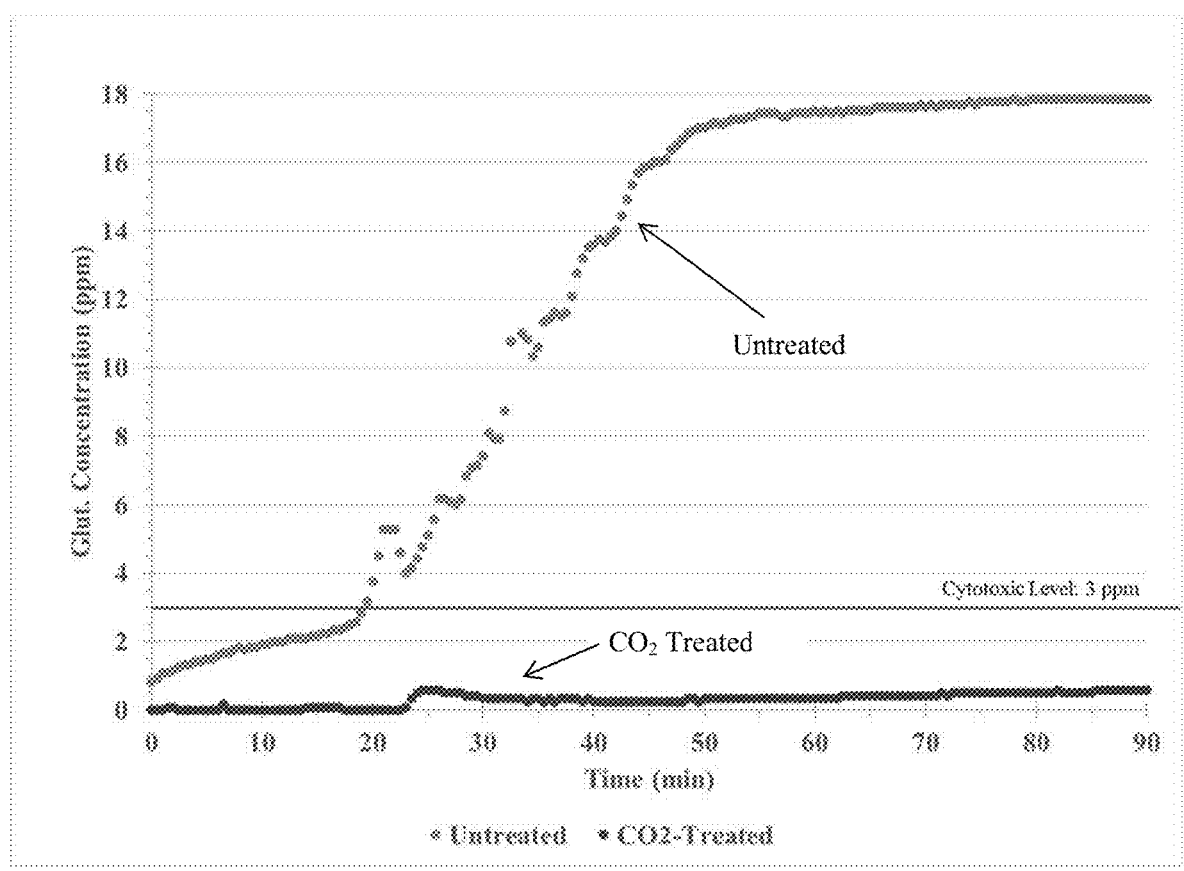
FIG. 2 compares the residual glutaraldehyde concentration in parts per million of collagen scaffolds treated with the cleaning solution of the present invention with the residual glutaraldehyde concentration in parts per million of untreated collagen scaffolds.

After the crosslinked collagen films were treated with supercritical $CO_2$, the concentration of the residual glutaraldehyde in the films was determined using absorbance measurements. Absorbance readings were converted into glutaraldehyde concentration using a standard curve. An example of transient glutaraldehyde release from collagen films before and after $CO_2$ treatment can be seen in FIG. 2. As shown, the concentration of glutaraldehyde plateaus after all residual glutaraldehyde has leached into the glycine solution. In this example, it is clear that the concentration of residual glutaraldehyde is far greater than the cytotoxic level of 3 parts per million (ppm) prior to $CO_2$ treatment. However, as also shown in FIG. 2, the $CO_2$ treatment extracts most of the unreacted glutaraldehyde, lowering the concentration to about 0.8 ppm.

Figure 3:
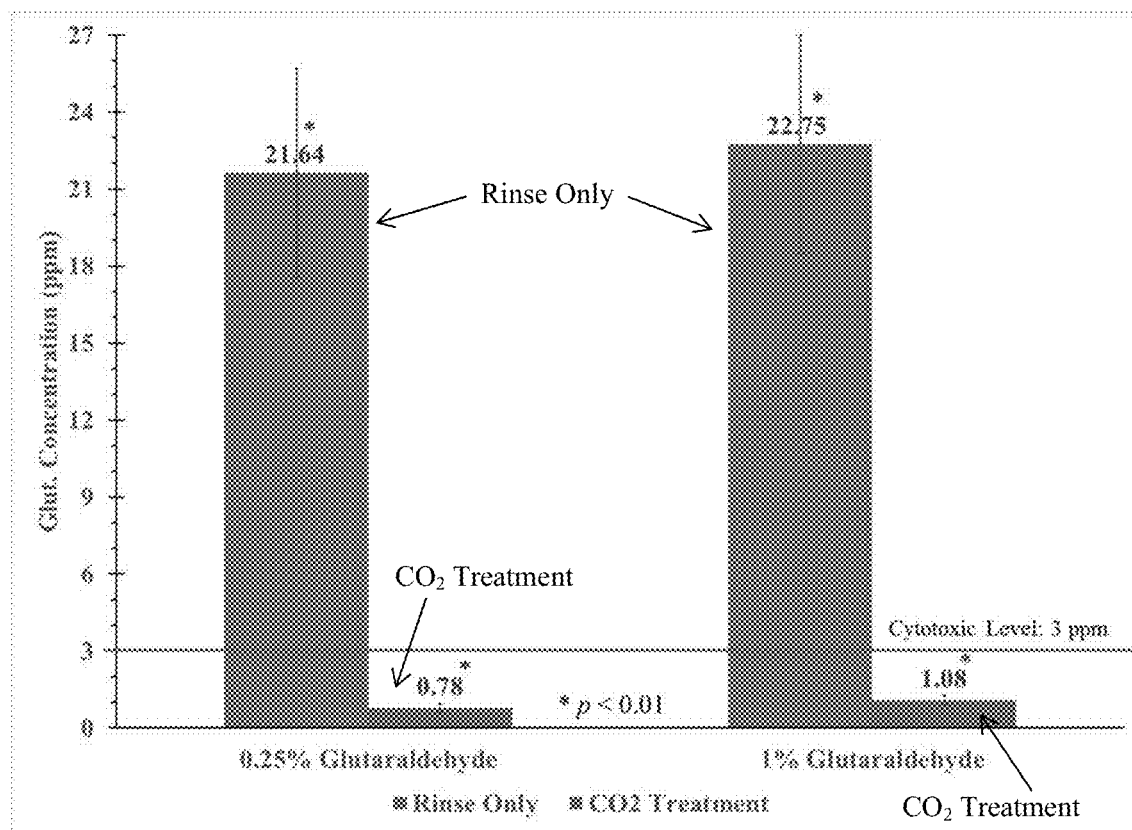
FIG. 3 compares the residual glutaraldehyde concentration in parts per million of collagen scaffolds treated with the cleaning solution of the present invention with the residual glutaraldehyde concentration in parts per million of untreated (deionized water rinse only) collagen scaffolds, where the scaffolds were crosslinked with a 0.25% glutaraldehyde solution and 1% glutaraldehyde solution.

Results of crosslinking for both crosslinking concentrations, 0.25% and 1%, can be seen in FIG. 3. First, as shown, the supercritical $CO_2$ and ethanol treatment solution extracts a significant amount of glutaraldehyde for both crosslinking treatments, thus reducing the residual glutaraldehyde levels well below the cytotoxic threshold (3 ppm) in both cases. Another interesting observation is that the concentration of residual glutaraldehyde both before and after supercritical $CO_2$ treatment is almost identical for 0.25% and 1% glutaraldehyde crosslinking solutions. This is counter-intuitive, since one would expect a direct correlation between the concentration of glutaraldehyde at the beginning and end of the crosslinking process.

However, there are several possible explanations for this result. One possibility is that increasing the concentration of the crosslinking solution may not affect how much glutaraldehyde enters the collagen matrix because of pore size and/or mass transfer limitations. Another possible explanation is that all of the glutaraldehyde reacts for both solutions, i.e. neither 0.25% nor 1% glutaraldehyde is a high enough concentration to fully crosslink collagen. Conversely, the opposite could also be true—if 0.25% glutaraldehyde fully crosslinks collagen, then increasing the concentration to 1% will have minimal effect. Glutaraldehyde is a five-carbon chain with aldehyde groups at each end. To crosslink, each aldehyde group reacts with the amine group on lysine, but on two separate collagen molecule. Lysine is not a frequently-occurring amino acid in the collagen molecule, so the number of available reaction sites is limited. Therefore, it is possible that the crosslinking reaction is limited by collagen and not by glutaraldehyde, meaning that increasing the glutaraldehyde concentration used for crosslinking will have no noticeable effect.

The validity of these theories, particularly those regarding reaction sites/extent of crosslinking, can be elucidated by studying the physical properties of the collagen films after supercritical $CO_2$ treatment. This was accomplished by studying thermal stability and mechanical properties, which are discussed in more detail below.

Physical Property Analysis

The primary concern with supercritical $CO_2$ treatment of biomaterials (e.g., natural polymer scaffolds such as collagen scaffolds) is inadvertent disruption of the biochemical or physical properties of the matrix. As such, the effect of supercritical $CO_2$ treatment on collagen film properties was evaluated using two analytical methods: (1) DSC to assess potential changes in thermal stability, and (2) uniaxial tensile testing to measure any alteration in stiffness or tensile strength.

The thermal stability of crosslinked collagen was studied using DSC, and the peak heights and denaturing temperatures in 4% acetic acid are listed in Table 1. As shown, crosslinked collagen has a much higher denaturation temperature than native collagen and a reduced denaturing peak height. Denaturation temperature increases because crosslinking increases thermal stability by introducing covalent bonds, requiring more energy to denature the protein. However, the peak height is reduced because short, non-crosslinked strands of collagen are able to unfold. Table 1 reveals that the supercritical $CO_2$ treatment of the present invention does not affect the thermal stability of crosslinked collagen, but heat treatment reduces peak height and denaturation temperature.

TABLE 1

Collagen DSC-Crosslinked Films, 4% Acetic Acid

| Film Type | Denaturation Temp. (° C.) | Peak Height (nW) |
| --- | --- | --- |
| Native | 39.1 ± 0.4 | 30.1 ± 8.4 |
| Crosslinked | 63.2 ± 0.2 | 10.0 ± 1.9 |
| Crosslinked + supercritical $CO_2$ | 63.3 ± 0.5 | 10.6 ± 2.5 |
| Crosslinked + 12 hour heat | 59.7 ± 2.7 | 3.9 ± 1.8 |

Figure 4:
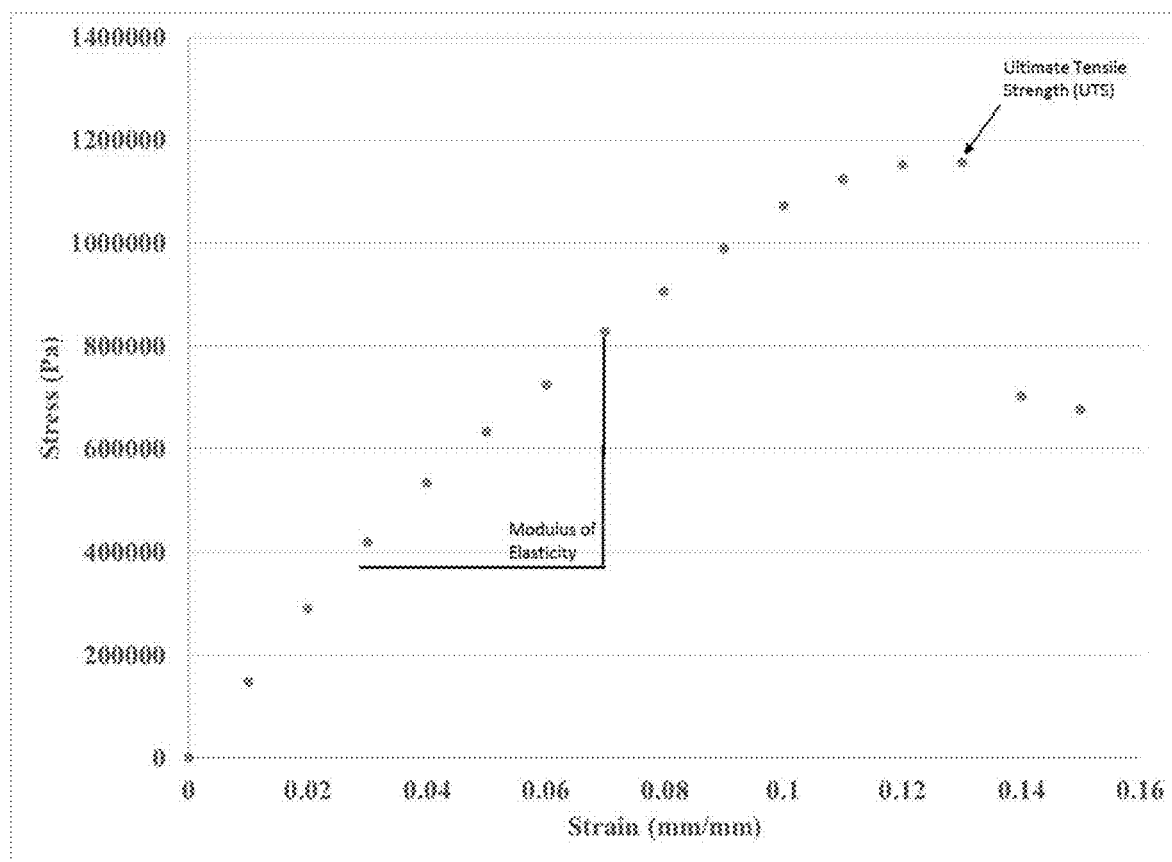
FIG. 4 shows a stress-strain curve for crosslinked collagen.

Untreated and crosslinked collagen films were also subjected to uniaxial tensile testing to determine the effects of crosslinking and supercritical $CO_2$ treatment on their MOE and UTS. An example stress-strain curve for crosslinked collagen is shown in FIG. 4. The modulus of elasticity is equal to the slope of the linear segment of the curve, the area of elastic, or reversible, deformation. As the strain increases, the linear segment ends and plastic, or irreversible, deformation begins. The point of maximum stress is the ultimate tensile strength, or UTS. At or shortly after this point comes fracture, indicated by a sharp decline in the stress value, going from 0.13 to 0.14 strain in the example shown in FIG. 4.

Average values for modulus of elasticity and ultimate tensile strength of each treatment can be viewed in Table 2.

TABLE 2

Collagen Film Tensile Test Data

| Treatment | Modulus (kPa) | UTS (kPa) |
| --- | --- | --- |
| Untreated | 838 ± 141 | 12.0 ± 2.7 |
| UV Crosslinked (4 hours) | 479 ± 101 | 24.3 ± 8.2 |
| Glutaraldehyde Crosslinked (72 hours) | 1113 ± 220 | 281 ± 30 |
| Glutaraldehyde + supercritical $CO_2$ | 1584 ± 404 | 1067 ± 211 |
| Glutaraldehyde + 12 hour heating | N/A* | N/A* |

It is clear the films have extremely low UTS prior to crosslinking. Crosslinking with UV irradiation increases the UTS about twofold. Though far from negligible, this increase is smaller than expected and does not indicate a high degree of crosslinking, a finding that echoes the DSC results. A 12 or 24 hour UV treatment may be needed to achieve greater extent of crosslinking. Surprisingly, the stiffness of the UV-treated fibers actually decreased somewhat, possibly indicating some kind of structural damage to the collagen film.

Glutaraldehyde crosslinking resulted in a much more dramatic increase in UTS, by about an order of magnitude, and a significant increase in modulus of elasticity was also found. These findings indicate a far greater extent of crosslinking than was observed during the UV treatment, again matching expectation and also confirming the DSC findings. The more interesting result is that of the $CO_2$-treated films.

Though no noticeable change in thermal stability was observed during DSC treatment, a highly significant increase in UTS was found in the tensile test data, and an increase in elastic modulus is also found. A likely explanation for this is related to potential dehydration of the collagen matrix because ethanol was used as a co-solvent during $CO_2$ treatment. Supercritical $CO_2$ is nonpolar, which makes it inert toward biomaterials, which are often charged and/or polar, under most circumstances. This is likely a significant factor in why little interaction is observed between native collagen and supercritical $CO_2$ during the performance of various assays. However, the addition of ethanol to increase glutaraldehyde extraction efficiency increases the polarity of supercritical $CO_2$ considerably; this combination is often used to intentionally remove water from sensitive materials during critical point drying.

The implications of biomaterial dehydration vary considerably depending on the material treated and the application. In some applications, such as scaffold production for long-term storage, a dry product is acceptable or even desirable. However, in a water-rich substrate like a hydrogel, this drying effect is potentially a major hindrance, so a method to prevent dehydration of biomaterials during supercritical $CO_2$ treatment can be applied to this system to prevent the drying phenomenon.

CONCLUSIONS

In the present example, a supercritical $CO_2$ method for extracting residual glutaraldehyde from crosslinked type I collagen films is demonstrated using the system 100 and method of the present invention. In only one hour of supercritical $CO_2$ treatment, over 90% of unreacted glutaraldehyde was removed from the films, reducing residual glutaraldehyde levels below 1 ppm, and well below the established cytotoxic limit of 3 ppm. Very similar results were obtained when 0.25% and 1% glutaraldehyde solutions were used to crosslink the films, likely because all possible reaction and sites were utilized even during the 0.25% glutaraldehyde treatment, making the increase in the concentration of the crosslinking solution superficial.

Differential scanning calorimetry and uniaxial tensile testing were performed to determine any potential effects of supercritical $CO_2$ treatment on the thermal and mechanical properties of the collagen films. DSC showed an extremely similar thermal response before and after supercritical $CO_2$ treatment in terms of both peak height and denaturation temperature, indicating that supercritical $CO_2$ treatment caused minimal disruption to the thermal stability of the films. Tensile testing showed a non-significant increase in stiffness compared to the control, but a highly significant increase in ultimate tensile strength, indicative of supercritical drying caused by the ethanol additive. Fortunately, this finding may not be problematic in some applications, and for applications where dehydration is a concern, biomaterial dehydration is easily preventable. In any event, the availability of a fast, innocuous method for removing residual glutaraldehyde from crosslinked collagen films overcomes a significant problem in the formation of collagen-based tissue engineered scaffolds.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed is:

1. A method for removing residual glutaraldehyde from a natural polymer scaffold, the method comprising:
    treating the natural polymer scaffold with a cleaning solution comprising carbon dioxide and one or more polar solvents at a temperature greater than 31.1° C., wherein the carbon dioxide is maintained at a pressure greater than 7.38 megapascals to form supercritical carbon dioxide, and wherein the one or more polar solvents comprises ethanol, methanol, isopropanol, acetic acid, or a combination thereof.

2. The method of claim 1, wherein a pump compresses the carbon dioxide before the carbon dioxide is delivered to the natural polymer scaffold.

3. The method of claim 1, wherein the carbon dioxide and the one or more polar solvents are mixed for a time period ranging from about 5 seconds to about 10 minutes prior to exposing the natural polymer scaffold to the cleaning solution.

4. The method of claim 1, wherein the cleaning solution is delivered to a treatment chamber containing the natural polymer scaffold.

5. The method of claim 4, wherein the cleaning solution is delivered to the treatment chamber at a flow rate ranging from about 1.5 millimeters per minute to about 3.5 milliliters per minute.

6. The method of claim 1, wherein the cleaning solution is mixed in a presaturation chamber, wherein the cleaning solution is delivered from the presaturation chamber to a treatment chamber containing the natural polymer scaffold.

7. The method of claim 1, wherein the natural polymer scaffold is exposed to the cleaning solution for a time period ranging from about 1 minute to about 2 hours.

8. The method of claim 1, wherein treating the natural polymer scaffold with the cleaning solution results in the natural polymer scaffold having a denaturation temperature of greater than about 60° C. in 4% acetic acid.

9. The method of claim 1, wherein treating the natural polymer scaffold with the cleaning solution results in the natural polymer scaffold having an ultimate tensile strength that is greater than about 40 kilopascals when the natural polymer scaffold includes collagen.

10. The method of claim 1, wherein the method facilitates removal of the residual glutaraldehyde from the natural polymer scaffold so that glutaraldehyde is present in the natural polymer scaffold at a level of less than about 3 parts per million after the natural polymer scaffold is treated with the cleaning solution.

* * * * *